United States Patent [19]

Gupta et al.

[11] Patent Number: 5,652,319
[45] Date of Patent: Jul. 29, 1997

[54] LOW-ODOR, HIGHER MOLECULAR WEIGHT POLYETHER POLYOLS, A PROCESS FOR PRODUCING THEM, AND THEIR USE FOR THE PRODUCTION OF POLYMERS, COSMETICS AND PHARMACEUTICAL PRODUCTS SYNTHESIZED FROM POLYETHER POLYOLS

[75] Inventors: Pramod Gupta, Bedburg; Gundolf Jacobs, Rösrath, both of Germany; Joél Leuridan, Antwerpen, Belgium

[73] Assignee: Bayer Aktiengesellschaft, Leverkusen, Germany

[21] Appl. No.: 700,718

[22] Filed: Aug. 13, 1996

[30] Foreign Application Priority Data

Aug. 18, 1995 [DE] Germany .................. 195 30 388.1

[51] Int. Cl.⁶ .................................................. C08G 18/32
[52] U.S. Cl. .................. 528/49; 528/76; 528/77; 568/679; 568/680

[58] Field of Search .................. 528/49, 76, 77; 568/679, 680

[56] References Cited

U.S. PATENT DOCUMENTS

| 3,653,183 | 4/1972 | Sanders et al. | 55/56 |
| 4,143,072 | 3/1979 | Hetzel et al. | 260/573 |
| 5,248,794 | 9/1993 | Choppell et al. | 568/679 |

FOREIGN PATENT DOCUMENTS

56-104936  8/1981  Japan .

*Primary Examiner*—Morton Foelak
*Attorney, Agent, or Firm*—Joseph C. Gil; N. Denise Brown

[57] ABSTRACT

Low-odor, higher molecular weight polyether polyols are produced by purifying the polyether polyols at temperatures of 110° to 150° C. and pressures of 10 to 70 hPa with the addition of 5 to 30% by weight of water, wherein the water is passed in finely divided form, with a droplet diameter of about 5 to 100 μ, through the polyether polyols to be purified for a time of metered addition of 1 to 5 hours.

5 Claims, No Drawings

LOW-ODOR, HIGHER MOLECULAR WEIGHT POLYETHER POLYOLS, A PROCESS FOR PRODUCING THEM, AND THEIR USE FOR THE PRODUCTION OF POLYMERS, COSMETICS AND PHARMACEUTICAL PRODUCTS SYNTHESIZED FROM POLYETHER POLYOLS

BACKGROUND OF THE INVENTION

The present invention relates to low-odor, higher molecular weight polyether polyols, a process for producing them, and their use for the production of polymers, cosmetics and pharmaceutical products synthesized from polyether polyols.

The industrial production of polyether polyols is generally by the alkoxylation of suitable starter compounds containing Zerewitinoff-active hydrogen atoms. This reaction yields a reaction mixture containing polyether polyols. However, the reaction mixture must be neutralized, dewatered and subsequently filtered to remove inorganic salts. Depending on the procedure used, the resultant polyether polyols contain from about 0.1 to 2% by weight of residual water, up to about 2% by weight of solvent (generally an organic solvent) and odoriferous substances such as aldehydes, dioxolanes, dioxanes, allyl alcohol, and mono-, di- and tripropylene glycol allyl ethers. Although these odoriferous substances are generally only present in small amounts, they nevertheless impart a characteristic, intense aromatic odor to the polyether polyols.

Various purification methods have therefore been developed and described in the art in order to remove unwanted by-products from polyether polyols which arise from their production. Thus, DE-A 2,755,089, for example, describes an improved process for removing troublesome by-products. This process specifically relates to removing small amounts of water and solvents, and also low molecular weight glycols and odor-intensive substances, by means of a spiral tube evaporator. A disadvantage of this process, however, is that the organic solvents which are present are not completely removed and the odor-intensive substances are removed only to a slight extent. Another disadvantage of the process described in this German patent, is the high cost of the apparatus associated therewith.

In principle, falling film evaporators can also be used for the purification of polyether polyols. However, they have the same disadvantages as the purification process by means of a spiral tube evaporator which is described in the above German patent.

Japanese Patent Application 56/104,936 describes a process for purifying polyether polyols in which, at a pH>6.5, either 1) the crude polyether polyols are distilled under reduced pressure and at elevated temperature, or 2) water, steam or nitrogen are passed through the crude polyether polyols, likewise under reduced pressure and at elevated temperature. However, as comparison example 2 of this Japanese Patent Applications shows, the troublesome odoriferous substances are only removed to an insufficient extent when passing water through the crude polyether polyol mixture. This is shown by the corresponding analysis results and odor tests. Moreover, the polyether polyols obtained from comparison example 2 were less durable, i.e. the aldehyde content of the polyether polyols increased, as did the unacceptable odor.

The object of the present invention was to provide polyether polyols, from which the odor-forming by-products have been removed to the greatest possible extent, so that these polyether polyols are practically odor-free. Practically odor-free polyether polyols such as these thus satisfy current requirements, particularly when they are used to produce polyurethanes and PU flexible foams which in turn are used in the production of furniture or mattresses. In addition, severe demands are imposed on the purity of polyether polyols used in the cosmetics industry, food packaging industry and in the pharmaceutical industry; the polyether polyols according to the invention are capable of complying with these demands, particularly being of neutral taste.

SUMMARY OF THE INVENTION

The present invention relates to a process for producing low-odor, higher molecular weight polyether polyols. This process comprises purifying the polyether polyols at temperatures of about 110° to 150° C., preferably about 115° to 140° C., and at a pressure of about 10 to 70 hPa, preferably about 20 to 50 hPa, with the addition of about 5.0 to 30.0% by weight, preferably about 7.0 to 25.0% by weight, of water, based on the quantity of polyether polyols present, wherein the water is passed in finely divided form with a droplet diameter of about 5.0 to 100µ, preferably about 7 to 50µ, through the polyether polyols to be purified for a time of metered addition of about 1 hour to 5 hours, preferably about 2 hours to 4 hours.

The present invention also relates to low-odor polyether polyols which are monofunctional or polyfunctional, and having molecular weights of from about 750 to 18,000, preferably about 1,000 to 15,000, and most preferably about 2,000 to 12,000, and a viscosity at 25° C. of from about 40 to 25,000, preferably about 50 to 10,000 mPa.s. These polyether polyols are produced by purifying the polyether polyols at temperatures of about 110° to 150° C. and at pressures of about 10 to 70 hPa, wherein about 5 to 30% by weight of water (based on the quantity of polyether polyols present) is metered into the polyether polyol over a time period of about 1 hour up to about 5 hours. The water which is metered into the polyether polyols is in finely divided form and has a droplet diameter of about 5 to 100µ.

This process results in purified polyether polyols which contain:

a) less than 1.5 ppm of 2-methyl-2-pentenal, preferably less than 0.2 ppm, b) less than 1.0 ppm of allyl alcohol, preferably less than 0.2 ppm, c) less than 15 ppm of allyloxypropanol, preferably less than 5.0 ppm, d) less than 50 ppm of dipropylene glycol allyl ether, preferably less than 0.5 ppm, and e) less than 1.0 ppm of propionaldehyde, preferably less than 0.2 ppm.

As used herein, the term molecular weight refers to the number average molecular weight. This is based on their OH number and functionality, and is readily calculated according to the formula:

$$MW = \frac{F \times 56,100}{OH\#}$$

wherein represents number average molecular weight of the polyether polyol,

F represents the functionality of the polyether polyol, and

OH# represents the OH number of the polyether polyol.

The viscosities herein are determined using a Höppler viscometer in accordance with DIN 53015.

The polyether polyols which are to be purified according to the invention are produced, as is known in the art, by the polymerization of epoxides, such as ethylene oxide, propylene oxide, butylene oxide, tetrahydrofuran, styrene oxide or epichlorhydrin with themselves, in the presence of acids for example, or by the addition of these epoxides, preferably in admixture or in succession, in the presence of acids or preferably of strong bases as catalysts, to starter components containing reactive hydrogen atoms. Some examples of starter components of this type include compounds such as n-butanol, n-hexanol, phenol, water, ethylene glycol, 1,2- and 1,3-propylene glycol, 1,4-butanediol, 4,4'-dihydroxydiphenylpropane, glycerine, trimethylolpropane, erythritol, sorbitol, ammonia, ethylenediamine, aniline, ethanolamine and triethanolamine. Sucrose polyethers, such as those which are described in, for example, German Auslegeschriften 1,176,358 and 1,064,938, and polyethers modified by vinyl polymers, such as those produced by the polymerization of styrene and acrylonitrile in the presence of polyethers (as described in, for example, U.S. Pat. Nos. 3,383,351, 3,304,273, 3,523,093 and 3,110,695, the disclosures of which are herein incorporated by reference, and in DE-B 1,152,536), can also be purified according to the present invention. Preferred polyether polyols are those which are based on ethylene oxide and/or propylene oxide, which contain 1 to 8, preferably 2 to 6 hydroxyl groups, and the molecular weights and viscosities of which fall within the ranges given above.

It is important for the process according to the invention that the metered addition of the water is effected during the purification of the polyether polyols such that the temperature does not fall below the lower temperature limit for distillation and the upper pressure limit is not exceeded. This is achieved by predetermination of the time required for the metered addition of the water which is to be added at a metered rate to the polyether polyols. If the predetermined distillation conditions are not adhered to, the odor-forming substances in the polyether polyols will only be removed to an insufficient extent.

As mentioned above, it is also important for the resultant purified polyether polyols of the present invention that the water be introduced into the polyether polyols in the form of very small droplets. This can be achieved, for example, by means of a capillary tube, a sintered metal frit or by means of fine pressure nozzles or pneumatic two-fluid nozzles.

It is preferred that good, intensive mixing of the distillation mixture occurs so that the water introduced comes into intimate contact with the polyether polyols to be purified. Known mixer devices, such as cross-arm agitators, grid agitators or ultrathorax mixers, can be used for this purpose.

The process according to the invention can be arranged downstream of the known polyether polyol production process as a separate purification step. It is also possible, of course, to subject commercially available polyether polyols in their unpurified form to subsequent purification using the process according to the invention, in order to obtain commercially available polyether polyols in a practically odor-free form.

The low-odor polyether polyols according to the invention can be used for the production of low-emission polymers synthesized from polyether polyols, such as polyurethanes, particularly polyurethane flexible foams, or elastomers, or for the production of cosmetics and pharmaceutical and food packaging products.

The invention is further illustrated but is not intended to be limited by the following examples in which all parts and percentages are by weight unless otherwise specified.

EXAMPLES

In the following examples, 1000 g of various polyether polyols (as described below) were heated to 120° C. 200 g water (20% by weight) were introduced at a pressure of 18 hPa via thin inlet tubes (diameter 0.2 mm) at a rate such that the temperature did not fail below 120° C. and the pressure did not rise above 40 hPa. The water was added to the unpurified polyether polyols over a time period of 3 hours. The water vapor bubbles had an average diameter of 7 to 50μ. Di- and trifunctional PO- and PO/EO polyethers were used in the examples. The effect of the purification according to the invention on the impurities in the polyether polyols used is apparent from Table 1. It can clearly be seen that after purification, the unwanted by-products, which amongst other effects resulted in the formation of an odor, were very extensively removed. Analysis was performed by means of head-space gas chromatography.

Polyether polyol 1: a glycerine started ethylene oxide/propylene oxide polyether which is branched, having an OH number of about 46, a molecular weight of about 3660 and a viscosity of about 560 mPa.s.

Polyether polyol 2: a propylene glycol started propylene oxide polyether which is linear, having an OH number of about 112, a molecular weight of about 1000 and a viscosity of about 140 mPa.s.

Polyether polyol 3: a propylene glycol started propylene oxide polyether which is linear, having an OH number of about 56, a molecular weight of about 2000 and a viscosity of about 310 mPa.s.

Polyether polyol 4: a trimethylolpropane started propylene oxide/ethylene oxide polyether which is branched, having an OH number of about 28, a molecular weight of about 6000 and a viscosity of about 1120 mPa.s.

TABLE 1

| | Example 1 Polyether polyol 1 | | Example 2 Polyether polyol 2 | |
|---|---|---|---|---|
| Compounds in the polyether polyols | before purification | after purification | before purification | after purification |
| 1,4-dioxan | <0,1 | <0,1 | <0,1 | <0,1 |
| 2,4-dimethyl-1,3-dioxolane | 1,5 | <0,1 | <0,1 | <0,1 |
| 2-ethylene-4-methyl-1,3-dioxolone | 2,5 | <0,1 | <0,1 | <0,1 |
| 2-methyl-2-pentenal | 1,8 | <0,1 | 2,2 | <0,1 |
| acetaldehyde | 1,2 | 0,1 | 1,9 | 2 |
| allyl alcohol | <0,1 | <0,1 | 0,6 | <0,1 |
| allyl oxypropanol | 80 | <0,1 | 0,6 | <0,1 |
| butyraldehyde | <0,1 | <0,1 | <0,1 | <0,1 |
| DPG allyl ether | 460 | <0,1 | 480 | <0,1 |
| propionaldehyde | 1,1 | 0,1 | 0,4 | 0,3 |
| sum of unknown readily volatile compounds | 20 | 8 | 15 | 8 |

(all data in ppm)

TABLE 2

| Compounds in the polyether polyols | Example 3 | | Example 4 | |
|---|---|---|---|---|
| | before purification | after purification | before purification | after purification |
| 1,4-dioxan | <0,1, | <0,1 | <0,1 | <0,1 |
| 2,4-dimethyl-1,3-dioxolane | <0,1 | <0,1 | <0,1 | <0,1 |
| 2-ethylene-4-methyl-1,3-dioxolone | 1,2 | <0,1 | <0,1 | <0,1 |
| 2-methyl-2-pentenal | 6 | 0,3 | 0,3 | <0,1 |
| acetaldehyde | 0,5 | 0,8 | 0,6 | 1,3 |
| allyl alcohol | 1,8 | <0,1 | <0,1 | <0,1 |
| allyl oxypropanol | 170 | 1,4 | 12 | 0,3 |
| butyraldehyde | <0,1 | <0,1 | <0,1 | <0,1 |
| DPG allyl ether | 650 | <0,1 | 55 | <0,1 |
| propionaldehyde | 2,7 | 0,1 | 0,3 | 0,3 |
| sum of unknown readily volatile compounds | 8 | 8 | 8 | 4 |

(all data in ppm)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the production of a polyurethane comprising reacting a polyisocyanate with an isocyanate-reactive component via the polyisocyanate polyaddition process, the improvement wherein said isocyanate reactive component comprises a low-odor, monofunctional or polyfunctional polyether polyol having a molecular weight of from about 750 to 18,000, and a viscosity at 25° C. of about 40 to 25,000 mPa.s, made by the process comprising 1) purifying polyether polyol at temperatures of about 100° to 150° C. and at pressures of about 10 to 70 hPa, wherein about 5 to 30.0% by weight of water, based on the quantity of polyether polyol present, is metered into said polyether polyol over a time period of about 1 hour up to about 5 hours, said water being in finely divided form and having a droplet diameter of 5 to 100μ, wherein the resultant polyether polyol contains a) less than about 1.5 ppm of 2-methyl-2-pentenal, b) less than about 1.0 ppm of allyl alcohol, c) less than about 15 ppm of allyloxypropanol, d) less than about 50 ppm of dipropylene glycol allyl ether, and e) less than about 1.0 ppm of propionaldehyde.

2. The process of claim 1, wherein said polyether polyol has a molecular weight of from about 1000 to about 15,000 and a viscosity of about 50 to 10,000 mPa.s at 25° C.

3. The process of claim 2, wherein said polyether polyol has a molecular weight of from about 2000 to about 12,000.

4. The process of claim 1, wherein about 7 to 25% by weight, based on the quantity of polyether polyol present, is metered into said polyether polyol over a time period of about 2 to 4 hours, said water having a droplet diameter of about 7 to 50μ.

5. The process of claim 1, wherein said distillation is at temperatures of about 115° to 140° C. and at pressures of about 20 to 50 hPa.

* * * * *